(12) United States Patent
Bianconi et al.

(10) Patent No.: US 9,060,716 B2
(45) Date of Patent: Jun. 23, 2015

(54) APPARATUS AND METHOD FOR ACQUIRING PANORAMIC, TELERADIOGRAPHIC AND OPTIONALLY VOLUMETRIC CBCT RADIOGRAPHIES

(71) Applicants: Davide Bianconi, Castel Guelfo di Bolonga (IT); Luca Guardini, San Bonifacio (IT); Dario Righini, Imola (IT)

(72) Inventors: Davide Bianconi, Castel Guelfo di Bolonga (IT); Luca Guardini, San Bonifacio (IT); Dario Righini, Imola (IT)

(73) Assignee: CEFLA SOCIETA COOPERATIVA, Imola (BO) (IT)

( * ) Notice: Subject to any disclaimer, the term of this patent is extended or adjusted under 35 U.S.C. 154(b) by 226 days.

(21) Appl. No.: 13/719,618

(22) Filed: Dec. 19, 2012

(65) Prior Publication Data
US 2013/0170612 A1    Jul. 4, 2013

(30) Foreign Application Priority Data
Dec. 28, 2011   (IT) .............................. BO2011A0764

(51) Int. Cl.
| *A61B 6/14* | (2006.01) |
| *A61B 6/00* | (2006.01) |
| *A61B 6/03* | (2006.01) |
| *A61B 6/04* | (2006.01) |

(52) U.S. Cl.
CPC ... *A61B 6/14* (2013.01); *A61B 6/04* (2013.01); *A61B 6/4007* (2013.01); *A61B 6/4085* (2013.01); *A61B 6/4441* (2013.01); *A61B 6/501* (2013.01); *A61B 6/588* (2013.01); *A61B 6/032* (2013.01)

(58) Field of Classification Search
None
See application file for complete search history.

(56) References Cited

U.S. PATENT DOCUMENTS

| 3,673,408 | A | * | 6/1972 | Moss | 378/39 |
| 4,323,779 | A | * | 4/1982 | Albert | 378/98.6 |
| 4,443,191 | A | * | 4/1984 | Gutierrez | 433/56 |
| 5,500,884 | A | * | 3/1996 | Guenther et al. | 378/38 |
| 5,511,106 | A | * | 4/1996 | Doebert et al. | 378/146 |
| 5,995,583 | A | * | 11/1999 | Schick et al. | 378/38 |
| 6,081,739 | A | * | 6/2000 | Lemchen | 600/407 |
| 6,829,326 | B2 | * | 12/2004 | Woods et al. | 378/38 |
| 7,092,483 | B2 | * | 8/2006 | Nyholm | 378/38 |
| 7,322,746 | B2 | * | 1/2008 | Beckhaus et al. | 378/205 |
| 7,424,091 | B2 | * | 9/2008 | Park et al. | 378/39 |
| 7,486,759 | B2 | * | 2/2009 | Suzuki et al. | 378/4 |
| 7,559,692 | B2 | * | 7/2009 | Beckhaus et al. | 378/205 |
| 7,715,525 | B2 | * | 5/2010 | Spartiotis et al. | 378/39 |
| 7,715,526 | B2 | * | 5/2010 | Spartiotis et al. | 378/39 |
| 7,742,560 | B2 | * | 6/2010 | Spartiotis et al. | 378/38 |
| 7,798,708 | B2 | * | 9/2010 | Erhardt et al. | 378/191 |
| 7,804,933 | B2 | * | 9/2010 | Nyholm | 378/39 |

(Continued)

FOREIGN PATENT DOCUMENTS

WO    9820796    5/1998

*Primary Examiner* — Andrew Smyth
(74) *Attorney, Agent, or Firm* — Cooper & Dunham LLP

(57) ABSTRACT

Apparatus and method for acquiring panoramic, teleradiographic and optionally CBCT volumetric dental radiographies, comprising a support holding a rotary arm which in its turn supports at one end a first X-ray source and at the other end an X-ray detector at a suitable distance for acquiring panoramic and optionally CBCT volumetric images. Apparatus comprises only one patient positioning system and a second X-ray source at a distance from detector suitable for acquiring cranial teleradiographies.

11 Claims, 2 Drawing Sheets

(56) References Cited

U.S. PATENT DOCUMENTS

| | | | |
|---|---|---|---|
| 8,005,186 B2 * | 8/2011 | Lee | 378/38 |
| 8,005,187 B2 * | 8/2011 | Suzuki et al. | 378/39 |
| 8,120,683 B1 * | 2/2012 | Tumer et al. | 348/295 |
| 8,152,373 B2 * | 4/2012 | Erhardt et al. | 378/191 |
| 8,306,181 B2 * | 11/2012 | Spartiotis et al. | 378/9 |
| 8,588,364 B2 * | 11/2013 | Suzuki et al. | 378/40 |
| 2003/0161438 A1 * | 8/2003 | Woods et al. | 378/19 |
| 2006/0227934 A1 * | 10/2006 | Beckhaus et al. | 378/98.8 |
| 2006/0233301 A1 * | 10/2006 | Erhardt et al. | 378/38 |
| 2007/0030951 A1 * | 2/2007 | Park et al. | 378/38 |
| 2008/0137802 A1 * | 6/2008 | Suzuki et al. | 378/4 |
| 2008/0144766 A1 * | 6/2008 | Beckhaus et al. | 378/21 |
| 2009/0168966 A1 * | 7/2009 | Suzuki et al. | 378/116 |
| 2009/0232274 A1 * | 9/2009 | Spartiotis et al. | 378/39 |
| 2009/0232275 A1 * | 9/2009 | Spartiotis et al. | 378/40 |
| 2009/0245461 A1 * | 10/2009 | Lee | 378/38 |
| 2009/0304148 A1 * | 12/2009 | Nyholm | 378/39 |
| 2010/0034340 A1 * | 2/2010 | Spartiotis et al. | 378/4 |
| 2010/0303204 A1 * | 12/2010 | Erhardt et al. | 378/62 |
| 2011/0064188 A1 * | 3/2011 | Suzuki et al. | 378/21 |
| 2011/0150185 A1 * | 6/2011 | Uzbelger Feldman | 378/191 |
| 2012/0314835 A1 * | 12/2012 | Muller | 378/16 |
| 2012/0321035 A1 * | 12/2012 | Muller | 378/4 |
| 2013/0307923 A1 * | 11/2013 | Inglese et al. | 348/36 |

* cited by examiner

APPARATUS AND METHOD FOR ACQUIRING PANORAMIC, TELERADIOGRAPHIC AND OPTIONALLY VOLUMETRIC CBCT RADIOGRAPHIES

BACKGROUND OF THE INVENTION

The present invention refers to the technical field of extraoral dental radiography, and particularly to a apparatus alternatively performing panoramic radiographies, cranial teleradiographies and optionally cone beam volumetric radiographies of facial skeleton. All these types of radiographies are well known in the art.

Panoramic radiography (also known as orthopantomography) produces a radiographic image of a curved plan approximating patient jaws, with blurring of the anatomical structures laying outside a narrow layer around the predesigned curved plane. This kind of acquisition is also indicated in the following with PAN.

Teleradiography is a projective radiographic technique, producing radiographic images of the skull or of other anatomical areas from different projections, with minimum magnification and geometrical distortion. Usually two perspectives are represented, latero-lateral and antero-posterior.

Cone beam volumetric radiography (also known as CBCT) is the acquisition, from different projection angles, of a series of two-dimensional radiographic images which will be processed post-acquisition to reconstruct three-dimensional volumes.

It is well known in the art that the positions of PAN, CBCT and teleradiographic sensors, and therefore the distance of the specific sensor from the X-ray source, are opportunely chosen so as to get the best radiographic result. The distance between X-ray source and X-ray sensor varies according to the kind of sensor. Generally speaking, the distance between teleradiographic sensor and X-ray source is the largest, while the distance between PAN sensor and X-ray source is smaller than the distance between CBCT sensor and X-ray source.

Indicatively, the distances allowing to get optimal radiographic results are the following:
X-ray source—PAN sensor distance: 520-580 mm;
X-ray source—CBCT sensor distance: 600-700 mm;
X-ray source—teleradiographic sensor distance: 1400-1600 mm.

Radiographic apparatuses acquiring panoramic and teleradiographic radiographies have been on the market for over 50 years. This kind of apparatuses generally has a C-arc, at whose ends the X-ray source and the X-ray detector are positioned at an appropriate distance to acquire panoramic images.

When a teleradiographic acquisition has to be performed, the X-ray detector must be positioned at a greater distance from the X-ray source than allowed by the dimension of the C arc. For this reason, such apparatuses are provided with a supplementary arm supporting the X-ray detector at an appropriate distance for performing teleradiography.

Traditionally, such apparatuses are provided with an X-ray source and at least one X-ray detector. When only one detector is present, this must be manually or automatically relocated in the desired position for panoramic or teleradiographic acquisition. When more than one detector is present, means for removing obstacles along the X-ray path between the X-ray source and X-ray detector for the specific acquisition are also present. One of the many examples of such apparatuses is Vatech's patent application WO200718332.

This kind of apparatus shows many drawbacks.

The first drawback lies in the high cost of X-ray detectors, which nowadays cost four-ten times the price of an X-ray source.

The second drawback, tightly linked to the first, lies in the fact that in the apparatuses provided with one X-ray detector only, which has to be manually relocated to perform the desired acquisition, there is a great risk of breakage, in that the X-ray detector is delicate and can undergo dangerous accidental falls during relocation. Moreover, in the apparatus removable connection systems must be provided, which must be safe under the point of view of electric transmission and reliable in the repeatability of positioning.

The third drawback lies in the fact that, due to acquisition geometry, on the same apparatus two different suitable patient positioning systems must be present, one for PAN/CBCT and one for teleradiography, with ensuing cost increase.

When during the same session a panoramic and a teleradiographic acquisition must be performed on the same patient (for instance an orthodontic patient), first the panoramic acquisition must be performed, then: in the simpler case of two X-ray detectors, the patient has to be moved from the first to the second patient positioning system; in the more complicate case of one X-ray detector only, the patient must be moved from the first to the second patient positioning system and the X-ray detector must be relocated. This leads to a significant prolonging of acquisition time for both operator and patient.

SUMMARY OF THE INVENTION

Aim of the present invention is providing an apparatus acquiring panoramic, teleradiographic and optionally CBCT volumetric images, having a simplified design and improved operations for both operator and patient, and of economic construction.

According to the present invention, there is provided an apparatus having two X-ray sources, each positioned at an opportune distance from an X-ray sensor, so that good quality images can be obtained. The X-ray detector can be the same for the three (panoramic, teleradiographic, volumetric) kind of acquisitions.

Obviously, in order to perform the desired (panoramic, teleradiographic or CBCT volumetric) acquisition, suitable means must be provided for removing the obstacles (X-ray sensor, collimator or X-ray source) from the X-ray path of the source used for the specific acquisition.

The X-ray detector can be an area sensor or a linear sensor.

In the case of an area sensor, which is the simplest and most suitable solution, teleradiography can be performed in one-shot mode, reducing emission time, patient dose and image elaboration. In this case it is sufficient to align the second X-ray source to the area X sensor, removing the first X-ray source from the second source X-ray path.

In the case of a linear sensor, in the art different methods are known to perform teleradiography requiring, or not, the movement of X-ray source during acquisition:

1) A first method, according to which the X-ray source remains essentially stationary during acquisition. The movement of the linear sensor is synchronous both with secondary collimator movement, and with a suitable primary collimator ensuring the irradiation of X-ray sensor during the entire acquisition.
2) A second method, according to which the X-ray source is suitably roto-translated to complete the acquisition. The movement of the linear sensor is synchronous with a secondary collimator integral with X-ray source. This method does not include the movement of primary collimator during acquisition.

In both cases the final image is a post-acquisition elaboration combining the plurality of linear images. In the present invention, when a linear sensor is to be used, both methods 1) and 2) can be used; obviously in the apparatus suitable means must be present to remove obstacles from X-ray path and for moving the second X-ray source in case 2).

BRIEF DESCRIPTION OF THE DRAWINGS

A non-limiting embodiment of the present invention will be now described by way of example with reference to the accompanying drawings, which show.

DETAILED DESCRIPTION OF THE INVENTION

Figure 1:
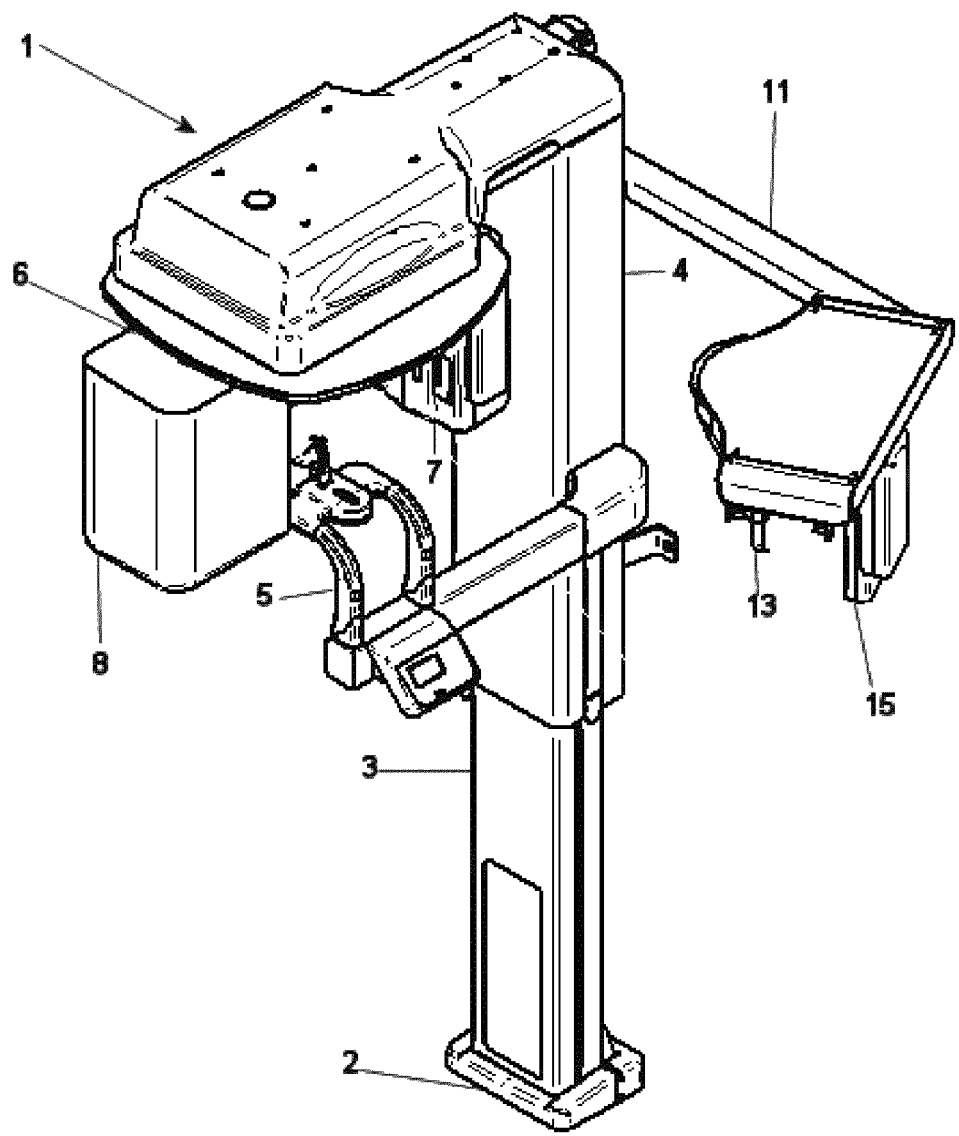
FIG. 1 a perspective schematic view of a prior art radiographic apparatus as a whole.

In FIG. 1, showing a prior art radiographic apparatus, 1 indicates on the whole an apparatus performing alternatively panoramic, teleradiographic and optionally CBCT volumetric acquisitions. Apparatus 1 comprises a base 2, a post 3 supporting an extension 4 which is provided with a vertical section sliding on the post 3 and a horizontal section. The vertical section of the extension 4 allows the vertical movement of a C-arm 6, which is attached to the horizontal section of the extension 4, and which in its turn supports an X-ray source 7, and an X-ray detector 8. In a more complete version of the apparatus, an alternating mechanism (not shown) is present, allowing to alternate a PAN sensor and a CBCT sensor. Moreover, a device 5 for the positioning of the patient is present.

On a further arm 11, arranged on extension 4, a support 12 for teleradiographic sensor 15 for teleradiography and a further device 13 for positioning the patient are present. In all acquisition modalities, the X-rays must hit the specific sensor: for the specific radiographic acquisition the sensor must be brought in the position allowing the hitting.

In FIG. 2, showing the present invention, the elements numbered 21 to 28 correspond to the same elements numbered from 1 to 8 in FIG. 1, while the elements numbered 201 to 207 represent the new elements according to the present invention with respect to FIG. 1.

Figure 2A:
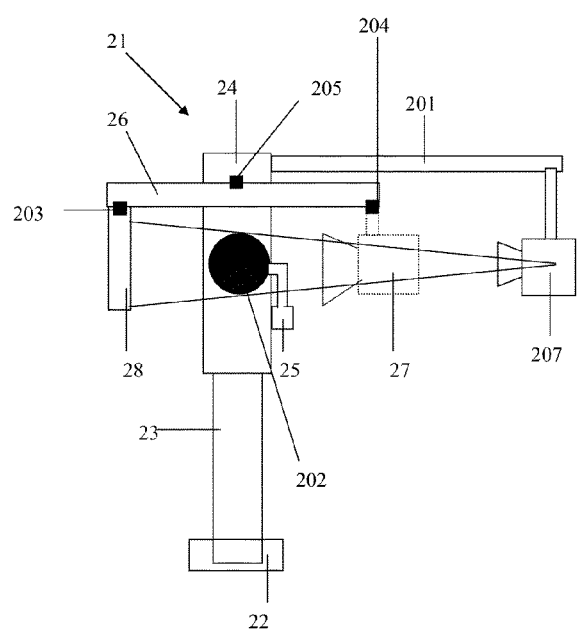
FIG. 2a a front view of the present invention apparatus as a whole.

In FIG. 2a, 21 indicates on the whole an apparatus alternatively performing panoramic, teleradiographic and optionally CBCT volumetric acquisitions.

Apparatus 21 comprises a base 22, a post 23 supporting an extension 24 which is provided with a vertical section sliding on the post 23 and a horizontal section. The vertical section of the extension 24 allows the vertical movement of a C-arm 26, which is attached to the horizontal section of the extension 24, and which in its turn supports a first X-ray source 27, and an X-ray detector 28. C-arm 26 is a rotary arm rotating around a patient skull 202, represented in a stylised form, during the acquisition of panoramic and CBCT volumetric images.

In a different apparatus configuration, performing CBCT volumetric acquisition in addition to panoramic acquisitions, means allowing to respect the optimal distance X-ray source—X-ray sensor during the respective acquisition have to be provided. In the preferred embodiment wherein only one X-ray sensor is present, means allowing to adjust the X-ray source—X-ray detector distance are provided.

In a different embodiment wherein two sensors are present, i.e. one PAN and one CBCT volumetric X-ray sensors, there is provided also an alternating mechanism allowing to alternate PAN and CBCT sensor.

Moreover, only one patient positioning device 25 is present.

In comparison to prior art, the new portion of the present invention is a second X-ray source 207, which is mounted on an arm 201 at a distance from patient 202 opportunely chosen to perform a cranial teleradiography. In the embodiment shown in the FIG. 2 the second X-ray source 207 is mounted on an arm 201 fixed on extension 24, but in other embodiments the arm 201 might be fixed to other portion of the apparatus or even to the wall.

Moreover, in FIG. 2a means 203 for moving X-ray detector 28 are shown. Said means 203 for moving X-ray sensor 28 can be used for:
1) adjustment of X-ray sensor 28—first X-ray source 27 during panoramic or volumetric acquisition;
2) alignment of X-ray sensor 28 with second X-ray source 207 during teleradiographic acquisition;
3) movement of X-ray sensor 28 in the case of a linear sensor during teleradiographic acquisition.

204 indicates means for moving the first X-ray source 27, which can be used for:
1) adjustment of X-ray sensor 28—first X-ray source 27 during panoramic or volumetric acquisition;
2) removal of first X-ray source 27 from X-ray path emitted by second X-ray source 207 during teleradiographic acquisition.

205 indicates means for moving the C-arm 26 to impart a correct inclination to C-arm 26 itself, allowing to remove obstacles from the X-ray path emitted by the second X-ray source 207 during teleradiography.

Moving means 203, 204, 205 can be present each alone, or in different combinations among them.

Figure 2B:
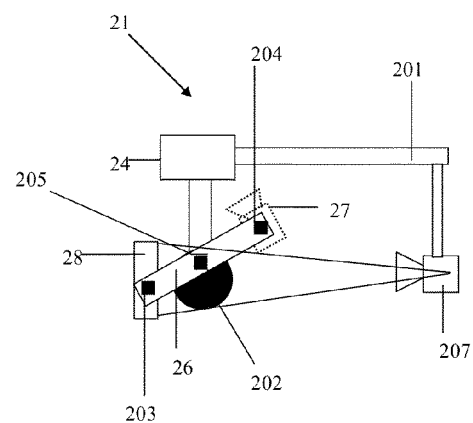
FIG. 2b a top view of the present invention apparatus as a whole.

FIG. 2b shows a top view of the same apparatus of FIG. 2a, in the preferred embodiment for performing a cranial teleradiography of a patient skull 202.

To perform a cranial teleradiography, the first X-ray source 27 must be removed from the X-ray path emitted from the second X-ray source 207. The configuration shown in FIG. 2b is preferred, wherein the X-ray detector 28 is an area sensor and therefore teleradiography can be acquired in standard mode (one-shot). Using different X-ray detectors is still possible, and consequently apparatus 21 configuration is to be modified for acquiring a cranial teleradiography.

In the preferred embodiment wherein only one area sensor is present, allowing to acquire panoramic, teleradiographic and optionally volumetric images, said area sensor is configured for the acquisition of panoramic images so that only a portion of the sensor area is sensitive to X-rays (PAN mode). Such portion corresponds to the area effectively hit by the X-ray beam emitted by the first X-ray source 27 during acquisition.

One of the advantages of the present invention lies in the possibility of using only one X-ray sensor opportunely chosen for all the three (panoramic, teleradiographic and CBCT volumetric) types of acquisition without the need to relocate it, therefore freeing the apparatus from the risk of damages during X-ray relocation. Such simplification allows to build a particularly cheap machine (presence of only one sensor, maximal simplicity of teleradiographic acquisition).

Another advantage of the present acquisition lies in the possibility of performing on the same patient during the same session both panoramic (or optionally volumetric) and teleradiographic acquisitions, without the need to relocate the patient in order to set up the apparatus. With the present apparatus, the patient is positioned only once on the only patient positioning system, and panoramic (and optionally volumetric) and teleradiographic acquisition can be performed in a row, only positioning the X-ray source and detector needed for the desired acquisition.

From the economic point of view, a further advantage of the present invention lies in the possibility of using different technologies for the X-ray source, using a rotating anode X-ray tube as the first X-ray source, more complex and expensive but with better performances especially for CBCT volumetric acquisitions, and a simpler and cheaper fixed anode X-ray tube as the second X-ray source for acquiring cranial teleradiographies.

1 apparatus
2 base
3 post
4 extension
5 patient positioning system
6 C-arm
7 X-ray source
8 X-ray detector
11 arm for teleradiography support
13 teleradiographic patient positioning system
15 teleradiographic sensor
21 new apparatus
22 base
23 post
24 extension
25 patient positioning system
26 C-arm
27 first X-ray source
28 X-ray sensor
201 arm for the second X-ray source
202 patient skull
203 means for moving X-ray sensor 28
204 means for moving first X-ray source 27
205 means for moving C-arm 26
207 second X-ray source

The invention claimed is:

1. Apparatus (21) for acquiring panoramic and teleradiographic radiographies and also capable of acquiring CBCT volumetric dental radiographies, comprising a support holding a rotary arm (26) which in its turn supports at one end a first X-ray source (27) and at the other end an X-ray detector (28) at a suitable distance for acquiring panoramic and/or CBCT volumetric images,
characterized in that
there is only one patient positioning system (25), and comprising a second X-ray source (207) at a distance from the X-ray detector (28) suitable for acquiring cranial teleradiographies, wherein the X-ray detector (28) is positioned and configured to be used to acquire at least panoramic and teleradiographic images;
wherein the first X-ray source (27) is configured to be removed from the X-ray path emitted by the second X-ray source; and
wherein the second x-ray source (207) and the X-ray detector (28) are configured to acquire teleradiographic images.

2. Apparatus according to claim 1, comprising only one X-ray detector (28).

3. Apparatus according to claim 1, wherein the X-ray detector is an area sensor.

4. Apparatus according to claim 3, wherein the area sensor is used in PAN mode for panoramic acquisitions and in standard mode for teleradiogranhic and CBCT volumetric acquisitions.

5. Apparatus according to claim 1, wherein the X-ray detector is a linear sensor.

6. Apparatus according to claim 1, wherein two X-ray detectors are present: one sensor for acquiring panoramic and teleradiographic images and one sensor for acquiring CBCT volumetric images, both sensors fixed on a mechanism allowing to alternate them.

7. Apparatus according to claim 1, wherein the first X-ray source (27) is a rotating anode X-ray tube.

8. Apparatus according to claim 1, wherein the second X-ray source is a fixed anode X-ray tube.

9. Apparatus according to claim 1, further comprising one or more devices chosen from the group consisting of: a device (203) for moving X-ray detector (28), a device (204) for moving the first X-ray source (27), a device (205) for moving C-arm (26), such device (205) having the aim of removing obstacles from the X-ray path between the second X-ray source (207) and X-ray detector (28).

10. Method for sequentially performing panoramic and teleradiographic and optionally CBCT volumetric acquisitions, using the device of claim 1, comprising the following steps:
positioning the patient in the only patient positioning device (25);
acquiring panoramic or CBCT volumetric images using the first X-ray source (27) and the X-ray detector (28);
removing the first X-ray source (27) from the X-ray path emitted by the second X-ray source (27); and
acquiring teleradiographic images using the second X-ray source (207) and the X-ray detector (28).

11. Apparatus (21) for acquiring panoramic, teleradiographic and optionally CBCT volumetric dental radiographies, comprising a support holding a rotary arm (26) which in its turn supports at one end a first X-ray source (27) and at the other end an X-ray detector (28) at a suitable distance for acquiring panoramic and optionally CBCT volumetric images,
characterized in that
there is only one patient positioning system (25), and comprising a second X-ray source (207) at a distance from the X-ray detector suitable for acquiring cranial teleradiographies, wherein the patient positioning system (25) is configured such that the patient remains in a single position when panoramic, teleradiographic and optionally CBCT volumetric images are acquired;
wherein the X-ray detector (28) is positioned and configured to be used to acquire at least panoramic and teleradiographic images;
wherein the first X-ray source (27) is configured to be removed from the X-ray path emitted by the second X-ray source (27); and
wherein the second X-ray source (207) and the X-ray detector (28) are configured to acquire teleradiographic images.

* * * * *